(12) United States Patent
Makarova et al.

(10) Patent No.: US 11,175,279 B2
(45) Date of Patent: Nov. 16, 2021

(54) POLYMER MICROFILTERS, DEVICES COMPRISING THE SAME, METHODS OF MANUFACTURING THE SAME, AND USES THEREOF

(71) Applicant: Creatv MicroTech, Inc., Potomac, MD (US)

(72) Inventors: Olga Makarova, Naperville, IL (US);
Cha-Mei Tang, Potomac, MD (US);
Peixuan Zhu, Derwood, MD (US);
Shuhong Li, North Potomac, MD (US);
Daniel Adams, Kensington, MD (US);
Platte T. Amstutz, Vienna, VA (US)

(73) Assignee: Creatv Microtech, Inc., Potomac, MD (US)

( * ) Notice: Subject to any disclaimer, the term of this patent is extended or adjusted under 35 U.S.C. 154(b) by 13 days.

(21) Appl. No.: 16/454,937

(22) Filed: Jun. 27, 2019

(65) Prior Publication Data
US 2019/0383794 A1    Dec. 19, 2019

Related U.S. Application Data

(63) Continuation-in-part of application No. 14/213,183, filed on Mar. 14, 2014, now abandoned, and a
(Continued)

(51) Int. Cl.
*G01N 33/50* (2006.01)
*B01D 71/46* (2006.01)
(Continued)

(52) U.S. Cl.
CPC ......... *G01N 33/5005* (2013.01); *B01D 29/00* (2013.01); *B01D 39/16* (2013.01);
(Continued)

(58) Field of Classification Search
CPC ............ G01N 33/5005; G01N 1/4077; G01N 1/4005; G01N 2001/4088; B01D 71/46;
(Continued)

(56) References Cited

U.S. PATENT DOCUMENTS

| 1,564,499 | A | 12/1925 | Tropp |
| 3,010,583 | A | 11/1961 | Kenyon |

(Continued)

FOREIGN PATENT DOCUMENTS

| CN | 1767898 A | 5/2006 |
| EP | 1031371 A1 | 8/2000 |

(Continued)

OTHER PUBLICATIONS

DuPont(TM) PerMX(TM) 3000 Photodielectric Dry Film Adhesive Technical Data Sheet.
(Continued)

*Primary Examiner* — Liam Royce
(74) *Attorney, Agent, or Firm* — Dickinson Wright PLLC

(57) ABSTRACT

A microfilter having a hydrophilic surface and suited for size-based capture and analysis of cells, such as circulating cancer cells, from whole blood and other human fluids is disclosed. The filter material is photo-definable, allowing the formation of precision pores by UV lithography. Exemplary embodiments provide a device that combines a microfilter with 3D nanotopography in culture scaffolds that mimic the 3D in vivo environment to better facilitate growth of captured cells.

9 Claims, 9 Drawing Sheets

Related U.S. Application Data continuation-in-part of application No. 13/696,139, filed as application No. PCT/US2011/030966 on Apr. 1, 2011, application No. 16/454,937, which is a continuation-in-part of application No. 16/400,600, filed on May 1, 2019, which is a continuation of application No. 13/854,003, filed on Mar. 29, 2013, now abandoned, which is a continuation-in-part of application No. PCT/US2012/066390, filed on Nov. 21, 2012.

(60) Provisional application No. 61/794,628, filed on Mar. 15, 2013, provisional application No. 61/330,819, filed on May 3, 2010, provisional application No. 61/377,797, filed on Aug. 27, 2010, provisional application No. 61/562,404, filed on Nov. 21, 2011, provisional application No. 61/618,641, filed on Mar. 30, 2012, provisional application No. 61/654,636, filed on Jun. 1, 2012.

(51) Int. Cl.
*G01N 1/40* (2006.01)
*B01L 3/00* (2006.01)
*B01D 39/16* (2006.01)
*B01D 29/00* (2006.01)
*B01L 9/00* (2006.01)

(52) U.S. Cl.
CPC ......... *B01D 39/1692* (2013.01); *B01D 71/46* (2013.01); *B01L 3/50* (2013.01); *B01L 3/5635* (2013.01); *B01L 9/00* (2013.01); *G01N 1/4005* (2013.01); *G01N 1/4077* (2013.01); *B01D 2239/0421* (2013.01); *B01L 3/502* (2013.01); *B01L 2300/0681* (2013.01); *G01N 2001/4088* (2013.01); *Y10T 29/49826* (2015.01); *Y10T 29/49963* (2015.01)

(58) Field of Classification Search
CPC .... B01D 39/1692; B01D 29/00; B01D 39/16; B01D 2239/0421; B01D 2239/10; B01L 3/5635; B01L 3/50; B01L 2300/0681; B01L 3/502; Y10T 29/49963; Y10T 29/49826
See application file for complete search history.

(56) References Cited

U.S. PATENT DOCUMENTS

| | | | |
|---|---|---|---|
| 3,505,180 A | 4/1970 | Brogden | |
| 4,454,749 A | 6/1984 | Guillemin et al. | |
| 4,777,021 A | 10/1988 | Wertz et al. | |
| 4,783,318 A | 11/1988 | Lapakko | |
| 4,840,698 A | 6/1989 | Kuehnert | |
| 5,049,268 A | 9/1991 | Kopf | |
| 5,059,659 A * | 10/1991 | Gregor | B01D 69/125 525/329.1 |
| 5,116,724 A | 5/1992 | Delaage et al. | |
| 5,221,483 A | 6/1993 | Glenn et al. | |
| 5,753,014 A | 5/1998 | Van Rijn | |
| 5,782,820 A | 7/1998 | Roland | |
| 5,792,354 A | 8/1998 | Aksberg | |
| 5,798,042 A | 8/1998 | Chu et al. | |
| 5,807,406 A | 9/1998 | Brauker et al. | |
| 5,916,626 A | 6/1999 | Moon et al. | |
| 5,932,100 A | 8/1999 | Yager et al. | |
| 6,241,886 B1 | 6/2001 | Kitagawa et al. | |
| 6,346,192 B2 | 2/2002 | Buhr et al. | |
| 6,463,656 B1 | 10/2002 | Debesis et al. | |
| 6,716,568 B1 | 4/2004 | Minsek et al. | |
| 2002/0041827 A1 | 4/2002 | Yager et al. | |
| 2002/0094303 A1 | 7/2002 | Yamamoto et al. | |
| 2002/0106643 A1 | 8/2002 | Kulseth et al. | |
| 2002/0122918 A1 | 9/2002 | Dentinger et al. | |
| 2002/0168839 A1 | 11/2002 | Yanagi et al. | |
| 2002/0187074 A1 | 12/2002 | O'Connor et al. | |
| 2003/0010708 A1 | 1/2003 | Leocavallo et al. | |
| 2003/0104359 A1 | 6/2003 | Cuthbertson et al. | |
| 2003/0138941 A1 | 7/2003 | Gong et al. | |
| 2003/0156992 A1 | 8/2003 | Anderson et al. | |
| 2003/0180807 A1 | 9/2003 | Hess et al. | |
| 2003/0213738 A1 | 11/2003 | Hiranaga et al. | |
| 2004/0036751 A1 | 2/2004 | Giere et al. | |
| 2004/0112213 A1 | 6/2004 | Dominiak et al. | |
| 2004/0131957 A1 | 7/2004 | Kubota et al. | |
| 2004/0182788 A1 | 9/2004 | Dorian et al. | |
| 2005/0048667 A1 | 3/2005 | Ellman et al. | |
| 2005/0073600 A1 | 4/2005 | Sato | |
| 2005/0074406 A1 | 4/2005 | Couvillon et al. | |
| 2005/0263452 A1 | 12/2005 | Jacobson | |
| 2005/0266335 A1 | 12/2005 | Johnson et al. | |
| 2006/0124865 A1 | 6/2006 | Wolfe et al. | |
| 2006/0133766 A1 | 6/2006 | Shelnut et al. | |
| 2006/0228873 A1 | 10/2006 | Liu et al. | |
| 2006/0228897 A1 | 10/2006 | Timans | |
| 2007/0025883 A1 | 2/2007 | Tai et al. | |
| 2007/0114207 A1 | 5/2007 | Hoffbauer et al. | |
| 2008/0023572 A1 | 1/2008 | Clark | |
| 2008/0063802 A1 | 3/2008 | Maula et al. | |
| 2008/0073600 A1 | 3/2008 | Appleby et al. | |
| 2008/0088059 A1 | 4/2008 | Tang et al. | |
| 2008/0169227 A1 | 6/2008 | Assion | |
| 2008/0164155 A1 | 7/2008 | Pease et al. | |
| 2008/0299695 A1 | 12/2008 | Ouellet et al. | |
| 2009/0042736 A1 | 2/2009 | Bomer et al. | |
| 2009/0073400 A1 | 3/2009 | Wolfe et al. | |
| 2009/0202813 A1 | 8/2009 | Itami et al. | |
| 2009/0232336 A1 | 9/2009 | Pahl | |
| 2009/0258318 A1 | 10/2009 | Chan | |
| 2009/0258791 A1 | 10/2009 | McDevitt et al. | |
| 2009/0297982 A1 | 12/2009 | Saitou et al. | |
| 2009/0321964 A1 | 12/2009 | Summerfelt et al. | |
| 2010/0003623 A1 | 1/2010 | Liu | |
| 2010/0038303 A1 | 2/2010 | Cai et al. | |
| 2010/0084747 A1 | 4/2010 | Chen et al. | |
| 2010/0089815 A1 | 4/2010 | Zhang et al. | |
| 2010/0122957 A1 | 5/2010 | Hongo et al. | |
| 2010/0129852 A1 | 5/2010 | Putnam et al. | |
| 2010/0255479 A1 | 10/2010 | Mikolajczyk et al. | |
| 2012/0037591 A1 | 2/2012 | Tringe et al. | |
| 2012/0168940 A1 | 7/2012 | Bieck | |

FOREIGN PATENT DOCUMENTS

| | | |
|---|---|---|
| EP | 2366449 A2 | 9/2011 |
| GB | 2392854 A | 3/2004 |
| JP | 5423139 A | 2/1979 |
| JP | 58-68899 U | 5/1983 |
| JP | 5868899 U | 5/1983 |
| JP | 60132803 U | 9/1985 |
| JP | 62121331 A | 6/1987 |
| JP | 3500003 A | 1/1991 |
| JP | 6500403 A | 1/1994 |
| JP | 6507375 A | 8/1994 |
| JP | 10508699 A | 8/1998 |
| JP | 2000237553 A | 9/2000 |
| JP | 2001299730 A | 10/2001 |
| JP | 2001324500 A | 11/2001 |
| JP | 2003194806 A | 7/2003 |
| JP | 2004212250 A | 7/2004 |
| JP | 2008000038 A | 1/2008 |
| WO | 8901966 A1 | 3/1989 |
| WO | 9200132 A1 | 1/1992 |
| WO | 9217110 A1 | 10/1992 |
| WO | 9513860 A1 | 5/1995 |
| WO | 9614563 A1 | 5/1996 |
| WO | 2008086477 A1 | 7/2008 |

(56) References Cited

FOREIGN PATENT DOCUMENTS

| WO | 20100085337 A1 | 7/2010 |
|---|---|---|
| WO | 2011139445 A1 | 11/2011 |

OTHER PUBLICATIONS

EMS Inc. Technical Data Sheet, DF-1014, Negative I-Line Dry Film Photoresist.

Jackman et al. "Microfluidic systems with on-line UV detection fabricated in photodefinable epoxy." Journal of Micromechanics and Microengineering [Online], 2001 [Retrieved on Aug. 4, 2011], vol. 11, pp. 263-269, Retrieved from the Internet: <URL:http://iopscience.iop.org/0960-1317/11/3/316., eso. 265-268.

Abgrall et al. "Lab-on-chip technologies: making a microfluidic network and coupling it into a complete microsystem—a review." Journal of Micromechanics and Microengineering [Online], 2007 [Retrieved on Aug. 5, 2011], vol. 17, pp. R15-R49, Retrieved from the Internet: <URL:http://iopscience.iop.org/0960-1317/17/5/R01:sessionid=BD3B04163976FCBOFD29F1D64FB90937.c1>, esp. pp. R28-R32.

International Search Report for International Application No. PCT/US11/30966, dated Aug. 17, 2011 (5 pages).

Written Opinion for International Application No. PCT/US11/30966, dated Aug. 17, 2011 (8 pages).

Hosokawa et al., High-Density Microcavity Array for Cell Detection: Single-Cell Analysis of Hematopoietic Stem Dells in Peripheral Blood Mononuclear Cells, Analytical Chemistry, vol. 81, No. 13, Jul. 1, 2009, p. 5308-5313.

Sharpe et al., Enumeration of High Numbers of Bacteria Using Hydrophobic Grid-Membrane Filters, Applied Microbiology, vol. 30, No. 4, Oct. 1975, p. 519-524.

\* cited by examiner (Sample: five30_004)

(Sample: Oxford30_005)

POLYMER MICROFILTERS, DEVICES COMPRISING THE SAME, METHODS OF MANUFACTURING THE SAME, AND USES THEREOF

This application is a continuation in part of, and claims priority to, the following prior applications the contents of all of which are hereby incorporated by reference herein: "POLYMER MICROFILTERS, DEVICES COMPRISING THE SAME, METHODS OF MANUFACTURING THE SAME, AND USES THEREOF", U.S. patent application Ser. No. 14/213,183, filed on Mar. 14, 2014 claiming priority to U.S. Provisional Patent Application No. 61/794,628, filed Mar. 15, 2013; "POLYMER MICROFILTERS AND METHODS OF MANUFACTURING THE SAME", U.S. patent application Ser. No. 13/696,139, filed on Nov. 5, 2012, which is a 371 of PCT/US11/30966, filed Apr. 1, 2011 claiming priority to two U.S. Provisional Patent Applications No. 61/330,819, filed May 3, 2010 and No. 61/377,797, filed Aug. 27, 2010; and "POLYMER MICROFILTRATION DEVICES, METHODS OF MANUFACTURING THE SAME AND THE USES OF THE MICROFILTRATION DEVICES", U.S. patent application Ser. No. 16/400,600, filed May 6, 2019, which is a continuation of U.S. patent application Ser. No. 13/854,003 filed on Mar. 29, 2013, which is a continuation in part of PCT/US12/66390 filed on Nov. 21, 2012, claiming priority to three U.S. Provisional Patent Applications No. 61/562,404 filed Nov. 21, 2011, No. 61/618,641 filed Mar. 30, 2012, and No. 61/654,636 filed Jun. 1, 2012.

BACKGROUND

Circulating tumor cells (CTCs) disseminated into peripheral blood from a primary or metastatic tumor can be used to phenotype and determine an organ of disease for diagnosis, to perform mutational studies to choose a targeted therapy, to monitor therapy effectiveness, to detect recurrence of disease, and to provide prognostic survival information of solid malignancies. Due to this wide variety of potential applications, a large number of techniques have been developed to enrich for CTCs. Enrichment/capture of CTCs is challenging, because of their extreme rarity, as few as 1 in 7.5 mL of blood containing $10^9$ blood cells. Since tumor cells are generally larger than blood cells, filtration of CTCs has been considered as long ago as 1964 by S. H. Seal of Memorial Sloan Kettering Cancer Center. In the past 15 years, filtration of CTCs has made significant advances. Even though it has been shown that filtration techniques are the most rapid and straightforward method to capture CTCs, filter choices were limited and less than ideal. At the present, track-etch polycarbonate filters are the only products commercially available for CTC applications. Track etch filters are used in products by ScreenCell® and Rarecells SAS. Since the pores in track-etch filters are distributed randomly, pores can overlap, resulting in variable pore size and low capture efficiency. Each track-etch filter is somewhat different from the others, so the standard deviation of capture is high. In an effort to minimize this pore overlap, porosity is typically kept low (3-5%), resulting in slow filtration and high nonspecific cell contamination on the filter.

Lithographic fabrication methods are able to produce uniform and precisely-patterned microfilters for CTC capture. This method has been accomplished in various academic settings using parylene, silicon, silicon nitride and nickel as the filter material. In each case, photolithographic membranes showed good clinical applicability when tested for CTC capture from patient blood samples. Most notable is parylene microfilters showing high CTC capture, which compared favorably against the classic CellSearch® CTC test (Veridex). Parylene material, however, is auto-fluorescent, and the parylene microfilters do not lie flat on microscope slides, complicating microscope imaging. Furthermore, the parylene filter fabrication method is a multi-step process, rendering it unsuitable for cost-effective volume production. The alternative membrane materials, including silicon, silicon nitride and nickel, are not transparent, the fabrication methods are hindered by high cost and limited scalability, which has prevented widespread testing, and clinical implementation is complicated. Further, as many of these materials are fragile or difficult to handle, support structures are needed to stabilize the membrane during filtration and analysis.

Given the limitations of existing filters, there is a need to develop new types of filters with improved characteristics. The present invention is directed to this and other important goals.

For some application, it is desirable for the microfilters to have surface treatment to (1) improving methods to attach antibodies, ligands, proteins, DNA, etc to the surface and (2) to produce nanosurface features. Some applications of nanosurface modifications are (a) changes the surface to be hydrophilic and (b) to enable 3D culture.

It is now understood and accepted that 2D culture induces cellular characteristics that differ significantly from those of tumors growing in vivo. It was shown that cell culture plates with 3D nanoimprinted scaffolds provide reproducible and significantly improved cell culture by facilitating cellular migration, intercellular adhesion, cellular viability, and proliferation, thus replicating the key features of tumors developing in vivo.

BRIEF SUMMARY

The present inventions is directed to microfilters having a hydrophilic surface that can be used to collect selected components, such as cells, from a fluid, such as a bodily fluid, including whole blood, urine, bone marrow, bladder wash, rectal brushings, fecal matter, saliva, cord blood, spinal and cerebral fluids, and other body fluids. The present inventions is also directed to the methods of using the microfilters in the removal and/or collection of materials, such as cells, from a fluid. The present invention is further directed devices comprising the microfilters, and to the methods of manufacturing the microfilters.

In a first embodiment of the present invention, a microfilter having a hydrophilic surface and suited for size based capture and analysis of cells, such as CTCs, from whole blood and other human fluids is provided. The filter material is photo-definable, allowing the formation of precision pores by UV lithography. The filter material is also subject to modification that results in at least one surface of the microfilter being hydrophilic. In one aspect of this embodiment, the invention is directed to a microfilter comprising a polymer layer formed from a photo-definable dry film, wherein a surface of the polymer layer is modified to be hydrophilic, and a plurality of apertures each extending through the polymer layer. In aspects of this embodiment, wherein the film is an epoxy-based photo-definable dry film. In aspects of this embodiment, the modification raises the surface energy of the polymer layer or produces a rough nanosurface on the polymer layer.

In further aspects of the first embodiment, the microfilter displays at least one analyte capture element on a surface of the polymer layer. The analyte capture element may comprise one or more of a polypeptide, nucleic acid, carbohydrate, and lipid. As a specific, non-limiting example, the analyte capture element may comprise an antibody with binding specificity for one or more of (i) EpCAM, (ii) MUC-1, (iii) both EpCAM and MUC-1, (iv) CD24, (v) CD34, (vi) CD44, (vii) CD133, and (viii) CD166.

In a second embodiment of the invention, a device that comprises a microfilter of the invention in a scaffold for use in tissue culture is provided. The device allows the 3D in vivo environment to be mimicked in vitro, thus better facilitating growth of captured cells. In aspects of this embodiment, such devices can facilitate a rapid, gentle, easy work flow to culture CTCs.

In a third embodiment of the invention, the following are provided: (a) methods to produce nanosurface structures on polymer sheets and films, and on polymer microfilters, that impart a hydrophilic characteristic to a surface of the sheet, film or microfilter, (b) applications to use nanosurface polymer materials for culturing cells, (c) culture plates and devices using the nanosurface sheets, films or microfilters for culture of cells, (d) applications of cell capture from body fluids with standard and nanosurface structured microfilters, and (e) coating of analyte capture elements on microfilters, and (f) applications of microfilters coated with analyte capture elements.

In a fourth embodiment, the present invention is directed to methods of using the microfilters of the invention in the collection of selected components from a fluid, such as a biological fluid. For example, in one aspect of this embodiment the invention is directed to a method of using a microfilter by passing a fluid through a plurality of apertures of a microfilter formed from an photo-definable dry film, wherein the microfilter has sufficient strength and flexibility to filter the fluid, and wherein the apertures are sized to allow passage of a first type of component in the fluid and to substantially prevent passage of a second type of component in the fluid. In a related aspect, the method further comprises collecting the second type of component in the fluid from the filter and performing one or more of identification, immunofluorescence, enumeration, sequencing, PCR, fluorescence in situ hybridization, mRNA in situ hybridization, other molecular characterizations, immunohistochemistry, histopathological staining, flow cytometry, image analysis, enzymatic assays, gene expression profiling analysis, erythrocyte deformability, white blood cell reactions, efficacy tests of therapeutics, culturing of enriched cells, and therapeutic use of enriched rare cells on the collected second component.

Fluids that might be used in conjunction with the methods include, but are not limited to, blood, urine, bone marrow, bladder wash, rectal brushings, fecal matter, saliva, cord blood, spinal and cerebral fluids, and other body fluids.

The second type of component in the fluid includes, but is not limited to, at least one member selected from the group consisting of: circulating tumor cells, tumor cells, epithelial-mesenchymal transition cells, CAMLs, white blood cells, B-cells, T-cells, circulating fetal cells in mother's blood, circulating endothelial cells, stromal cells, mesenchymal cells, endothelial cells, epithelial cells, stem cells, hematopoietic and non-hematopoietic cells, analytes bound to latex beads or an antigen-induced particle agglutination.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION

Figure 1:
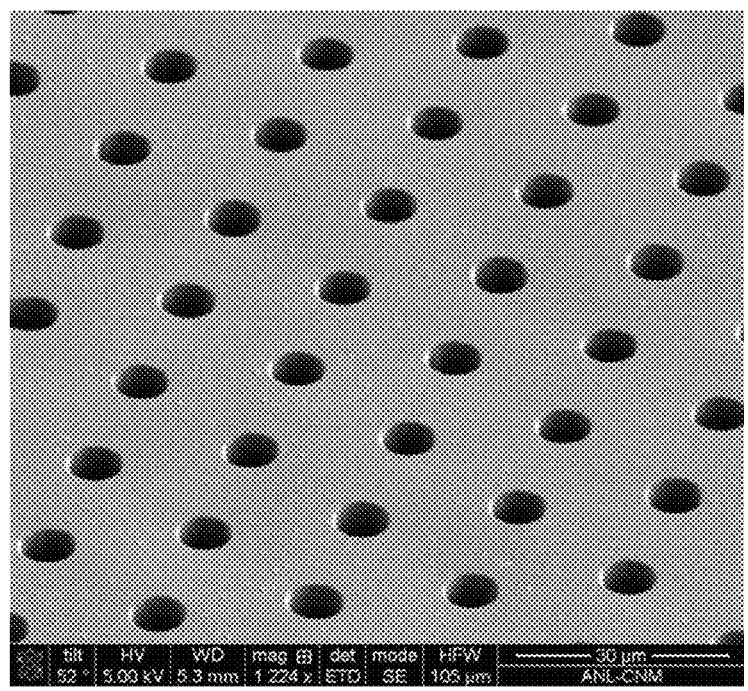
FIG. 1 is scanning electron micrograph (SEM) showing an example of microfilter fabricated based on the method and material described in the cross reference patents.

Referring now to the drawings, wherein like reference numerals designate identical or corresponding parts throughout the several views, exemplary aspects of the present invention are shown in schematic detail.

The matters defined in the description such as a detailed construction and elements are nothing but the ones provided to assist in a comprehensive understanding of the invention. Accordingly, those of ordinary skill in the art will recognize that various changes and modifications of the exemplary aspects described herein can be made without departing from the scope and spirit of the invention. Also, well-known functions or constructions are omitted for clarity and conciseness. Some exemplary aspects of the present invention are described below in the context of commercial applications. Such exemplary implementations are not intended to limit the scope of the present invention, which is defined in the appended claims Aspects of the present invention are generally directed to a microfilter comprising a polymer layer formed from a photo-definable dry film, such as an epoxy-based photo-definable dry film. The microfilter includes a plurality of apertures each extending through the polymer layer. Further, the polymer layer is modified to be hydrophilic. In certain exemplary aspects, the microfilter may be formed by exposing the dry film to energy through a mask and developing the exposed dry film. In some exemplary aspects, the dry film may be exposed to energy in the form of ultraviolet (UV) light. In other exemplary aspects, the dry film may be exposed to energy in the form of X-rays. In certain exemplary aspects, the polymer layer has sufficient strength and flexibility to filter liquid. In some exemplary aspects, the apertures are sized to allow passage of a first type of bodily fluid cell and to prevent passage of a second type of bodily fluid cell.

According to exemplary implementations of the present disclosure, a microfilter can comprise a polymer layer formed from an epoxy-based negative photo-definable dry film. According to further exemplary implementations of the present disclosure, the apertures of the microfilter can be essentially of any shape or configuration such as round, oval, racetrack, or rectangle, or any combination thereof. In yet other exemplary aspects, the polymer layer of the microfilter can have a uniform thickness of 5 to 100 microns. In still further exemplary aspects, the polymer layer of the microfilter can have a uniform thickness of 10 μm. In yet further exemplary aspects, the apertures can round with a diameter of 5-20 μm. Any combinations of such polymer layer, aperture features and configurations are within the scope for a microfilter structure of the present disclosure.

Specifically, in certain exemplary aspects, the microfilter may be used to perform assays on bodily fluids. In some exemplary aspects, the microfilter may be used to isolate and detect large rare cells from a bodily fluid. In certain exemplary aspects, the microfilter may be used to collect circulating tumor cells (CTCs) from peripheral blood from cancer patients passed through the microfilter. In certain exemplary aspects, the microfilter may be used to collect circulating endothelial cells, fetal cells and other large cells from the blood and body fluids. In certain exemplary aspects, the microfilter may be used to collect large cells from processed tissue samples, such as bone marrows. In some exemplary aspects, cells collected using the microfilter may be used in downstream processes such as cell identification, enumeration, characterization, culturing, etc.

More specifically, in certain exemplary aspects, multiple layers of photo-definable dry film, such as an epoxy-based photo-definable dry film, may be exposed to energy simultaneously for scaled production of microfilters. In some exemplary aspects, a stack of photo-definable dry film layers is provided, and all of the dry film layers in the stack are exposed to energy simultaneously. In some exemplary aspects, a dry film structure including photo-definable dry film disposed on a substrate is provided in the form of a roll. In such exemplary aspects, a portion of the structure may be unrolled for exposure of the dry film to energy. In certain exemplary aspects, portions of a plurality of rolls may be exposed to energy simultaneously.

FIG. 1 is scanning electron micrograph (SEM) of microfilter fabricated based on the known techniques. The surface is smooth, shiny and hydrophobic. The contact angle is approximately 90 degrees. The hydrophobic property of the material allows performing assays with reagents staying above the filter without the reagents leaking through. However, the hydrophobic nature of the filter is also problematic when it is desired to have a filter through which fluids easily pass, e.g., a microfilter with hydrophilic surface characteristics. For some applications, it is desirable to modify a surface of the microfilter to have hydrophilic characteristics via, for example, increasing the surface energy of a surface of the microfilter and/or altering the surface topography of a surface of the microfilter through various methods of surface treatment.

Surface Modification Methods and Resultant Microfilters

The surface of a microfilter may be modified to impart a hydrophilic characteristic through methods of surface treatment. The most common methods of surface treatment are based on a principle of high voltage discharge in air without changing the topography of the surface. When the microfilter is placed in the discharge path, the electrons generated in the discharge impact the surface creating reactive free radicals. These free radicals in the presence of oxygen can react rapidly to form various chemical function groups on the microfilter surface. This raises the surface energy of the microfilter. It changes the microfilter from hydrophobic to hydrophilic. Surface treatment can improve wettability of the microfilter by raising the material's surface energy and positively affect adhesive characteristics by creating bonding sites. An example of high voltage discharge is corona discharge.

Some of the applications of microfilters treated by corona discharge are: (i) flow of fluid through small pores with less resistance, (ii) cell morphologies may be better preserved when the use of small pores are required, (iii) better conjugation of analyte capture elements to the microfilter, (iv) attachment of various surface modification materials, and others.

Four additional methods of surface treatment are provided herein that produce surface modifications on polymer microfilters and that serve to increase the hydrophilicity of the surface: (a) reactive ion etching, (b) energetic neutral oxygen atoms etching, (c) reactive ion etching through anodic aluminum oxide (AAO) template, and (d) surface imprinting. These methods make a surface of a polymer layer rougher in texture. The 3D surface features produced by each method are different but they share the characteristic that the surface of the polymer layer that has undergone treatment is rougher in texture than the surface prior to treatment. As with microfilters using polymer layers with surfaces treated using corona discharge, microfilters using polymer layers with surfaces treated to alter the 3D surface features also exhibit (i) increased flow of fluid through small pores with less resistance, (ii) better preservation of cell morphologies, (iii) better conjugation of analyte capture elements to the microfilter, and (iv) improved attachment of various surface modification materials.

Reactive Ion Etching (RIE) Method.

Figure 2A:
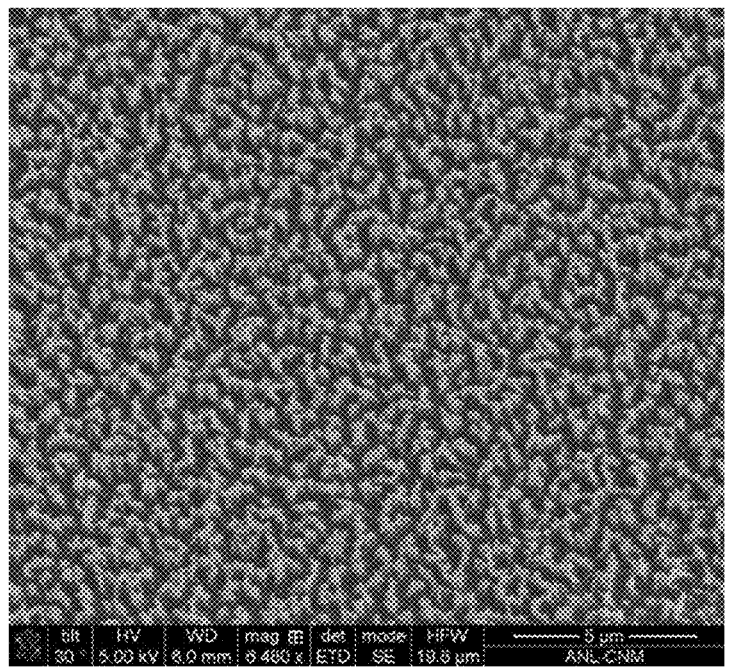
FIGS. 2A-2D show examples of nanoscale features on polymer surfaces etched by ME.
Figure 2B:
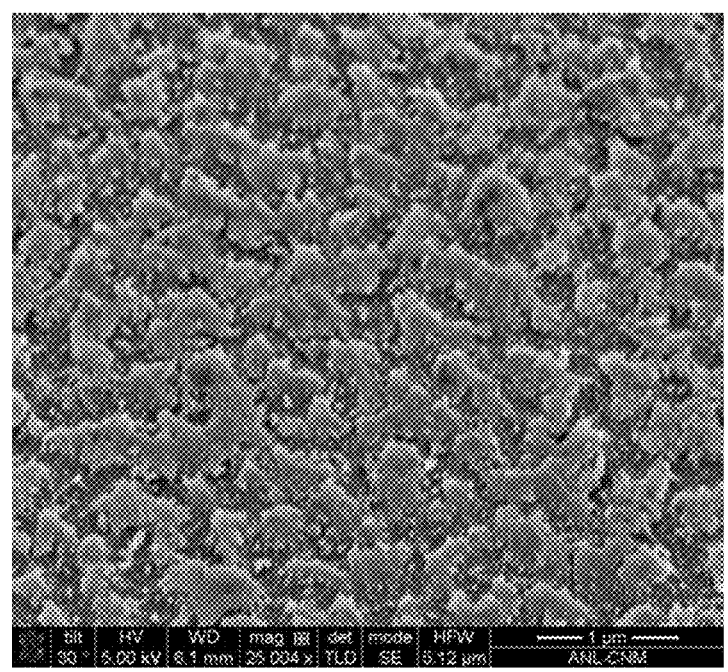
Figure 2C:
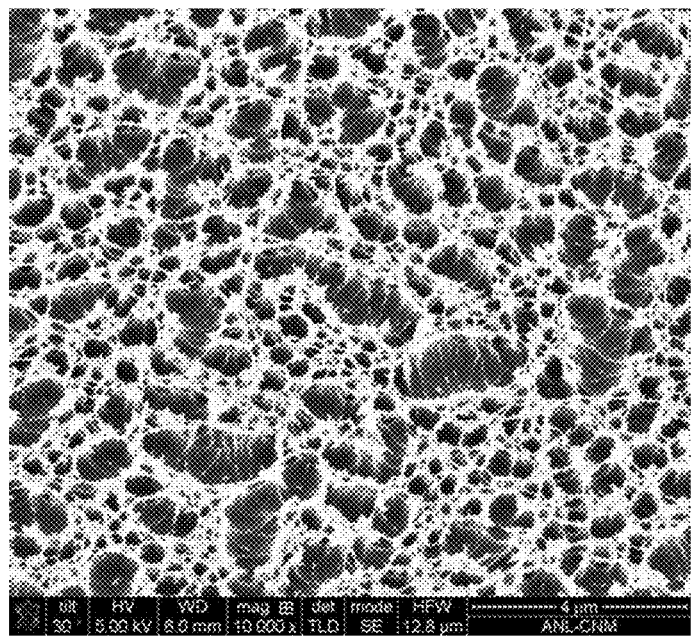
Figure 2D:
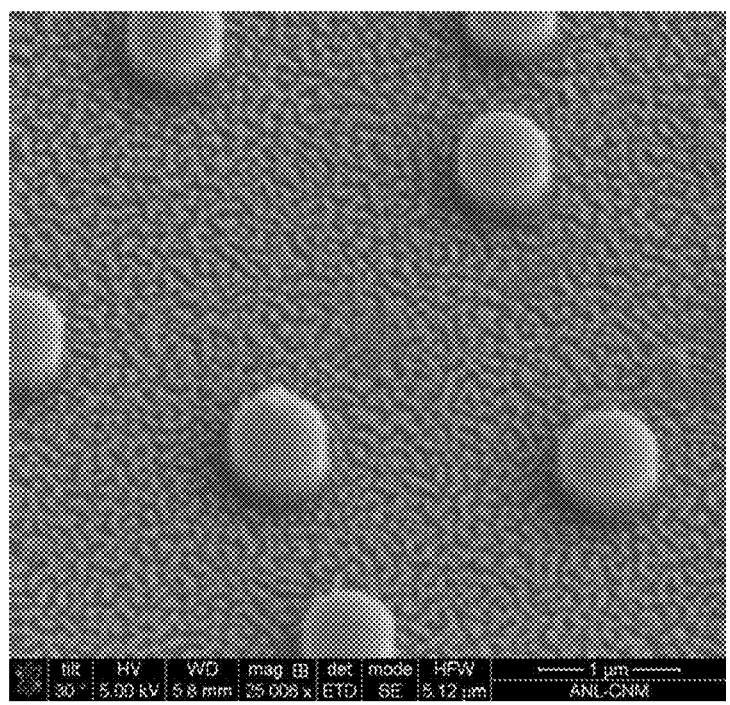

RIE utilizes chemically reactive plasma (high-energy ions) to remove material from the surface of a polymer layer. This results in the creation of a rough nanosurface on the polymer layer. Variations in the resulting etching of the surface are achieved depending on the material to be etched and on the settings of RIE parameters. FIGS. 2A-D are scanning electron micrographs (SEMS) of examples of surface modifications produced by RIE on photo-definable dry-film without pores. FIG. 2D shows nanostructures with two different length scales.

Figure 3:
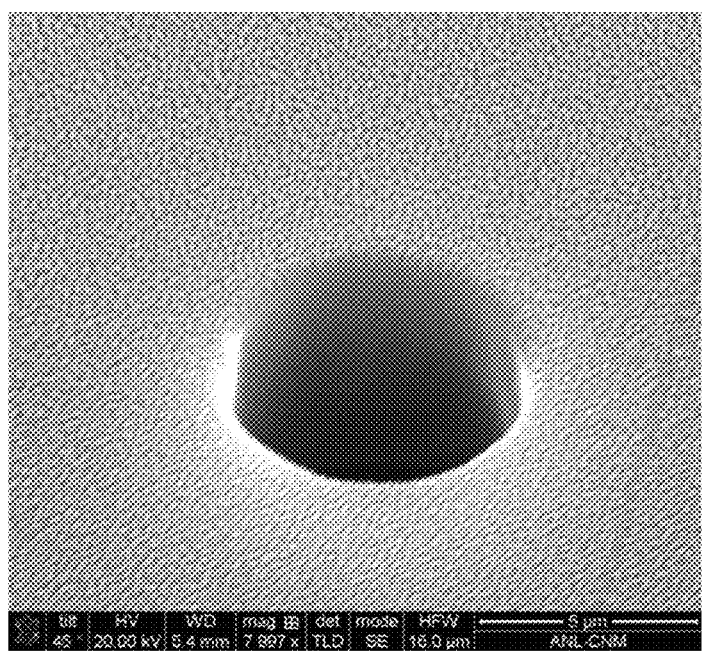
FIG. 3 shows an example of a microfilter after ME showing a pore and nanosurface topography.

RIE can be applied to microfilters, such as track etch microfilters, parylene microfilters, microfilters produced from photo-definable dry films, any filters made by polymer material as well as made from silicon wafers. FIG. 3 shows a SEM of a microfilter fabricated based on the method and material described in the cross reference patents, followed by treatment by RIE showing nanosurface topography and a pore.

The surface treated by RIE becomes hydrophilic. The contact angle is almost zero.

Energetic Neutral Oxygen Atom Etching.

Figure 4:
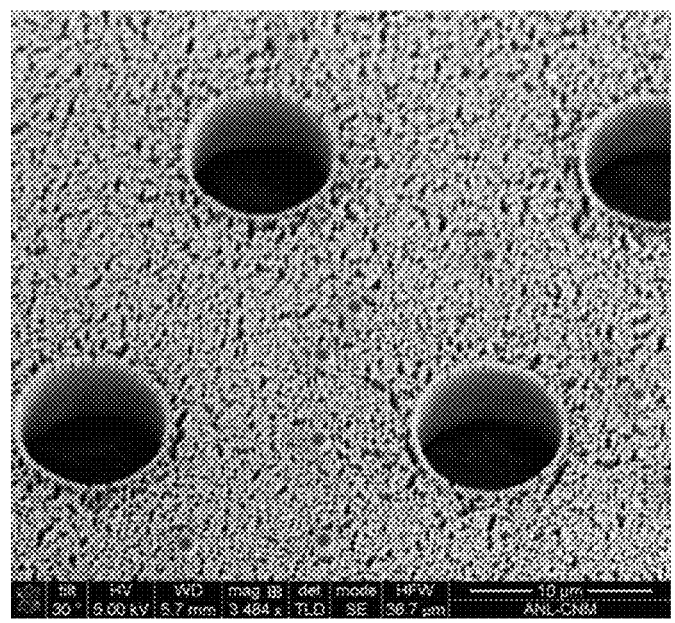
FIG. 4 shows an example of a microfilter after energetic neutral oxygen atom etching showing pores and nanosurface topography.

Another method to produce a rough nanosurface on a polymer layer is to apply energetic neutral oxygen atom etching on the polymer surface with or without pores. To create a rough nanosurface on microfilters, energetic neutral oxygen atom etching is performed after the microfilters are already formed but still attached to substrate. FIG. 4 shows SEM of a microfilter treated by energetic neutral oxygen atoms showing nanosurface topography and pores.

RIE Through a Nanoporous AAO Mask.

Figure 5A:
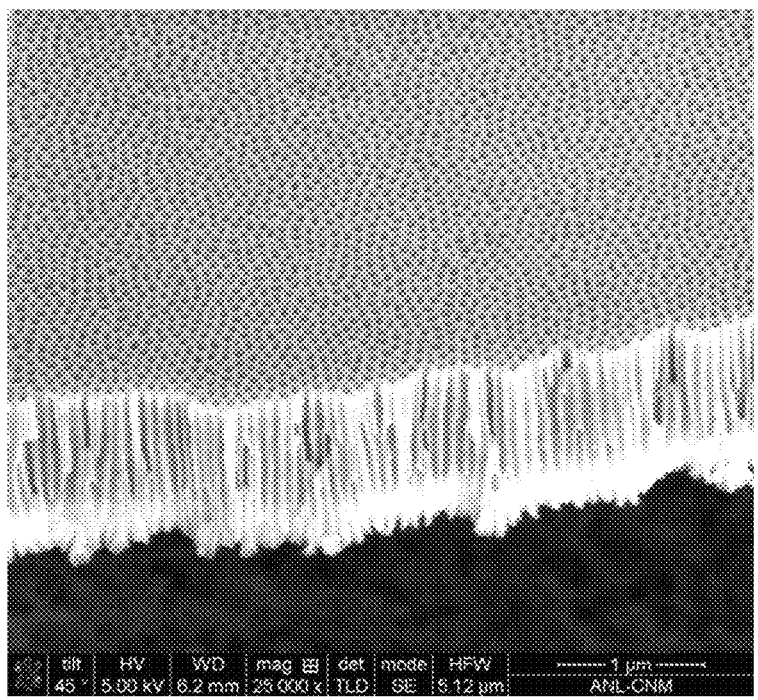
FIG. 5A shows an example of an anodic aluminum oxide (AAO) template formed above a polymer substrate. AAO has nanopores.
Figure 5B:
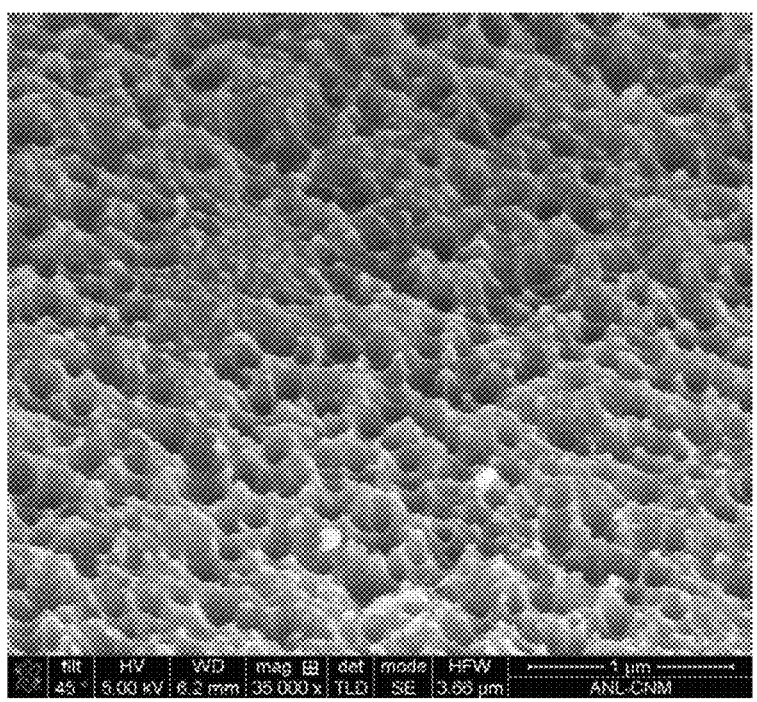
FIG. 5B shows an example of polymer surface after RIE through AAO.

Another method to produce a rough nanosurface on a polymer layer using a porous metal material as a mask. (i) One example of a mask is to utilize AAO. AAO template is fabricated on the resist surface by deposition and anodizing of ~1 μm-thick Al film according to recipe. FIG. 5A is a SEM of the AAO template above the surface of the polymer material. Surface relief is obtained by RIE via AAO template followed by AAO removal in phosphoric acid solution. SEM of the resultant nanosurface structure is shown in FIG. 5B. (ii) Another group of porous materials for RIE are micro magnetic beads and glass beads.

Nanoimprinting.

Figure 6:
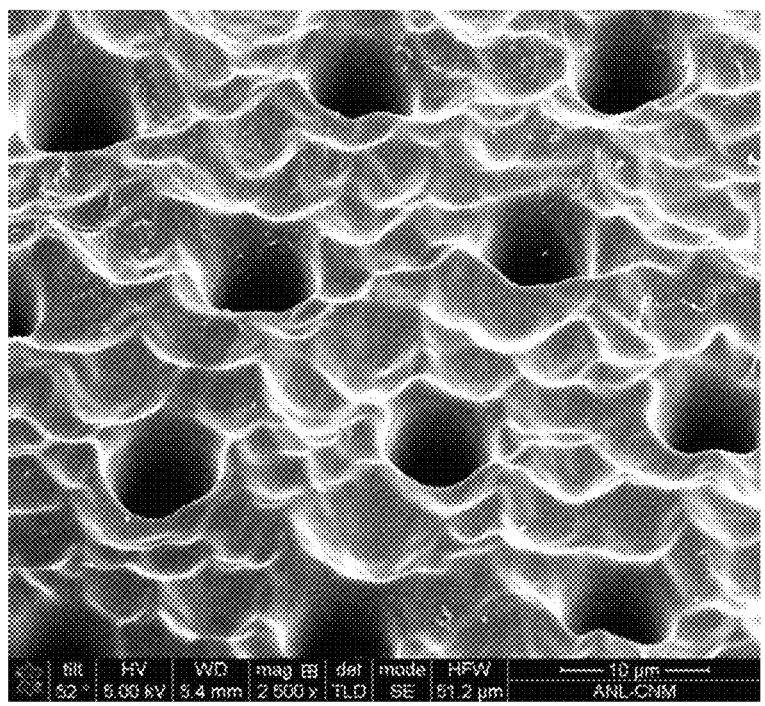
FIG. 6 shows an example of nanoscale surface topography microfilter with pores produced by imprinting using rough metal surface as the mold.

Another method to produce a rough nanosurface on a polymer layer is by imprinting the dry film on nanostructured surface. Using photo-definable dry films for microfilters, the substrate with rough nanosurface can be used. FIG. 6 is an SEM of microfilter produced by imprinting the dry film on the rough metal substrate. The nanosurface features is directly dependent on the mold.

Figure 7:
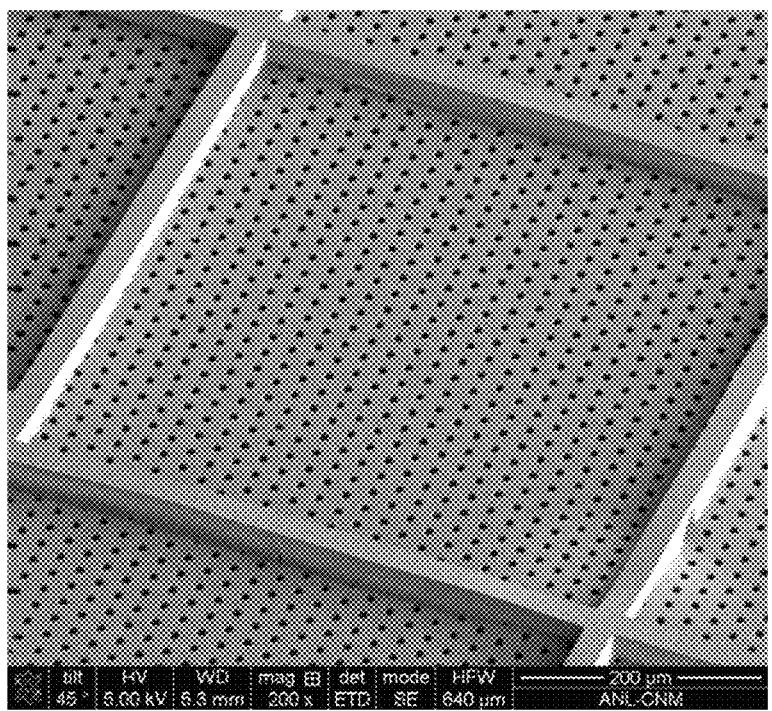
FIG. 7 shows an example of lithographically produced microwells on top of a microfilter.

For some applications, it is desirable to have wells formed above the microfilters. For example of culture of cells in their individual well. A method to form the wells consists of laminated photo-definable dry films on surface of filter material with pores already formed. Microfilter-culture wells are fabricated using UV lithography, followed by development. After a hard bake, the microfilter device with wells can be released from substrate. FIG. 7 shows an SEM of a microfilter with square wells.

3D Culture

Cell culture properties are highly dependent on the type of cell. It has been shown that some cells growing in culture in clumps (3D) express different markers than the same cell line grown in a flat layer (2D) on the culture plate. There has been a lot of research on finding conditions for 3D culture. A bladder cancer cell line, T24, was selected to illustrate the effect of 2D and 3D culture.

When the microfilters or polymer materials of the present invention were coated with fetal bovine serum (FBS) and bovine serum albumin (BSA), the bladder cancer cell line T24 grew similar to culturing on the standard culture chamber slide. However, if FBS or BSA can be eliminated, the culture process can be simplified.

Figure 8A:
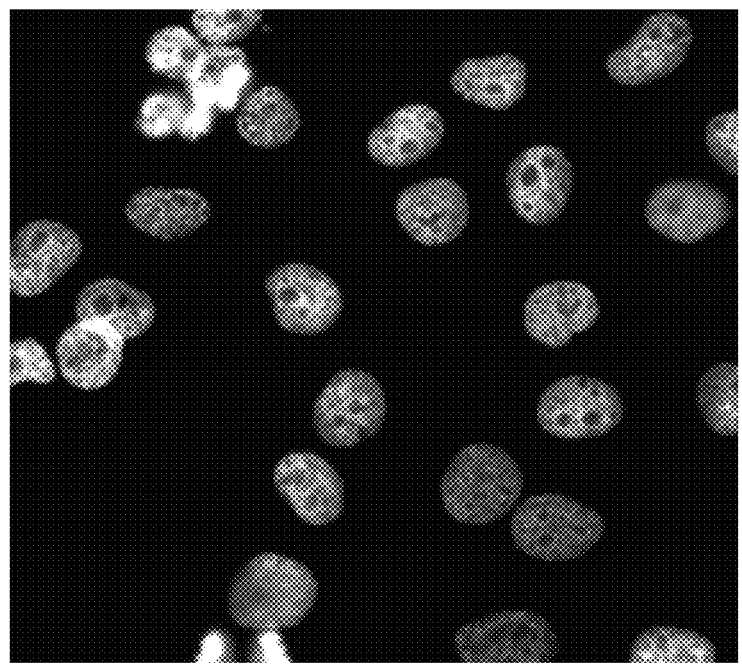
FIG. 8A shows an example of T24 cell culture on chamber slide showing DAPI nucleus in white on black background.
Figure 8B:
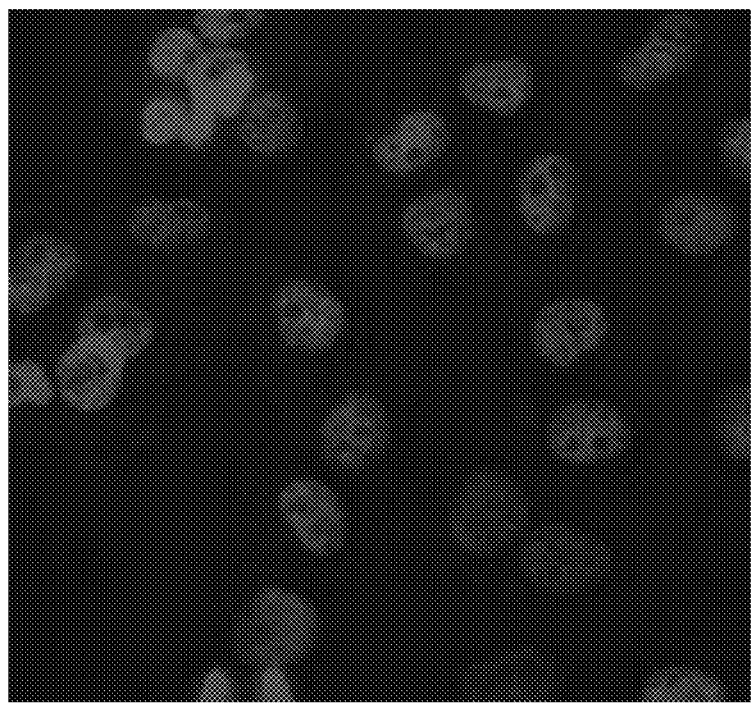
FIG. 8B shows the same T24 cell culture on chamber slide showing a merged color image of DAPI nucleus in blue and cytokeratin (CK) 8 and 18 in green. The CK expression is very weak.

When the polymer materials or microfilters of the present invention are uncoated, the T24 culture results become very different. FIG. 8A shows the microscope imaging of the nuclei stained by DAPI of T24 cells grown on chamber slide. The cells grew flat in 2D format. The cells are imaged after permeabilized and stained by cytokeratin (CK) 8 and 18 conjugated to FITC dye. FIG. 8B shows the microscope imaging combining DAPI (blue) and CK 8, 18 (green). The cells show very low or no CK 8 and 18.

When T24 cells were cultured on photo-definable dry film polymer not treated by RIE, T24 cells grew in 2D format similar to the results of chamber slide.

Figure 9A:
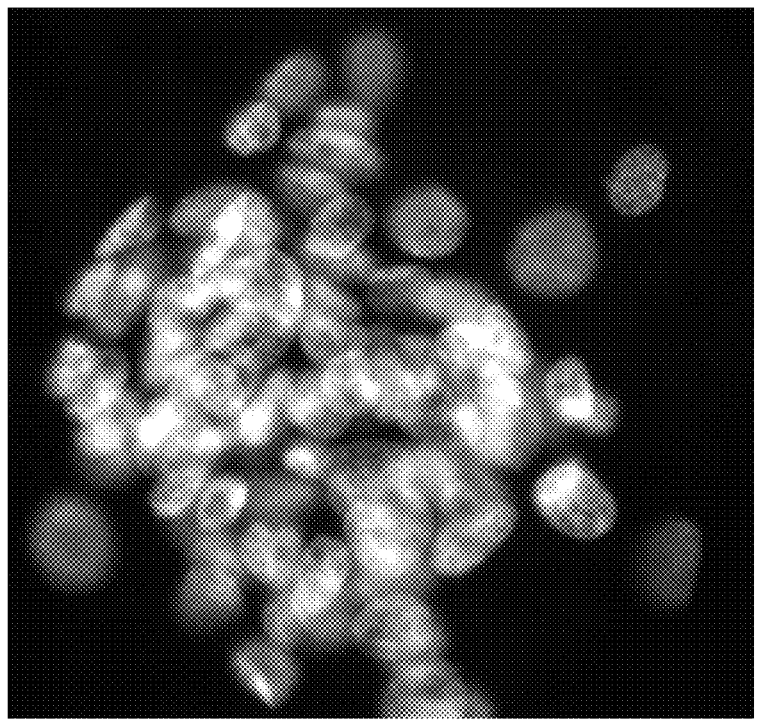
FIG. 9A shows an example of T24 cell culture on RIE treated photo-definable dry film showing DAPI nucleus in white on black background in the form of a cluster.
Figure 9B:
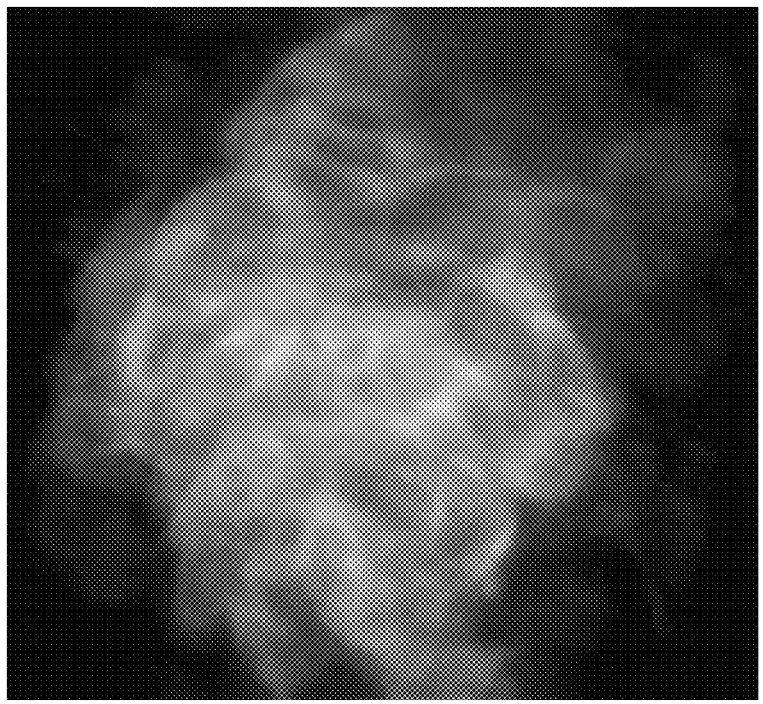
FIG. 9B shows the same T24 cell culture on RIE treated photo-definable dry film showing a merged color image of DAPI nucleus in blue and CK 8 and 18 in green. The CK expression is high.

In contrast, T24 cells grew in 3D clumps on photo-definable dry film polymer treated by low dose RIE. FIG. 9A shows the microscope imaging of the clump of nuclei stained by DAPI of T24 cells grown on ME treated films. The cells are permeabilized and stained by cytokeratins (CK) 8 and 18 conjugated to FITC. FIG. 9B shows the microscope imaging combining DAPI (blue) and CK 8, 18 (green). The cells show very strong CK 8, 18.

It was also found that when cells were spiked into PBS followed by filtration using RIE treated microfilter, FIG. 3, the cells grew in a 3D format.

In summary, it has been shown that the photo-definable dry film polymer treated with ME enabled 3D culture, and that the 3D cultured cells behaved differently than 2D cultured cells.

Culture Plates and Devices

Devices to implement 3D culture on chamber slides, and 6, 12, 24, 96 and 384 well culture plates were prepared. Some variations of implementation are possible.

Place RIE etched polymers on the bottom of these wells. This includes RIE etched photo-definable dry film polymer.

Place RIE etched polymers on the bottom of these wells coated with FBS or BSA. This includes RIE etched photo-definable dry film polymer.

Place RIE etched microfilters on the bottom of these well. This includes RIE etched photo-definable dry film microfilter.

Place RIE etched microfilters on the bottom of these well coated with FBS or BSA. This includes RIE etched photo-definable dry film microfilter. This includes RIE etched photo-definable dry film microfilter.

Place fibroblast cells, fibroblast cell fragments, other cells, other cell fragments, or other culture reagents on the bottom of the culture wells. Place RIE etched microfilters above that.

Cells can be captured on the RIE etched microfilter before placing into culture plates.

Cells can be captured on FBS coated microfilters before placing into culture plates.

Coating of Smooth Microfilters and Nanosurface Microfilters with Analyte Capture Elements As used herein, the term "analyte" is intended to mean a biological particle. Biological particles include, for example, cells, tissues, or organisms as well as fragments or components thereof. Specific examples of biological particles include bacteria, spores, oocysts, cells, viruses, bacteriophage, membranes, nuclei, golgi, ribosomes, polypeptides, nucleic acid and other macromolecules. "Analyte complex" is intended to mean a biological particle or a group of biological particles connected to analyte capture coating and/or other components, such as proteins, DNA, polymers, optical emission detection reagent, etc.

"Analyte capture" coating or elements are useful for selectively attaching or capturing a target analyte to microfilter. Attachment or capture includes both solid or solution phase binding of an analyte to an analyte capture element. An analyte is attached or captured through a solid phase configuration when the analyte capture coating or element is immobilized to a microfilter when contacted with an analyte. An analyte is attached or captured through a solution phase configuration when the analyte capture coating or element is in solution when contacted with an analyte. Subsequent immobilization of a bound analyte-analyte capture coating or element complex to a microfilter completes attachment or capture to the microfilter. In either configuration, either direct or indirect immobilization of the analyte capture coating or element to a microfilter can occur. Direct immobilization refers to attachment of the analyte capture coating or element to a microfilter allowing for capture of an analyte from solution to a solid phase. Immobilization of the analyte capture coating or element can be directly to a microfilter surface or through secondary binding partners such as linkers or affinity reagents such as an antibody. Indirect binding refers to immobilization of the analyte capture coating or element to a microfilter. Analyte capture elements can form an analyte capture complex and become attached to the analyte capture surface on the microfilter.

Moieties useful as an analyte capture coating or element in the invention include biochemical, organic chemical or inorganic chemical molecular species and can be derived by natural, synthetic or recombinant methods. Such moieties include, for example, macromolecules such as polypeptides, nucleic acids, carbohydrate and lipid. Specific examples of polypeptides that can be used as an analyte capture coating or element include, for example, an antibody, an antigen target for an antibody analyte, receptor, including a cell receptor, binding protein, a ligand or other affinity reagent to the target analyte. Specific examples of nucleic acids that can be used as an analyte capture coating or element include, for example, DNA, cDNA, or RNA of any length that allow sufficient binding specificity. Accordingly, both polynucleotides and oligonucleotides can be employed as an analyte capture coating or element of the invention. Other specific examples of an analyte capture coating or element include, for example, ganglioside, aptamer, ribozyme, enzyme, or antibiotic or other chemical compound. Analyte capture coatings or elements can also include, for example, biological particles such as a cell, cell fragment, virus, bacteriophage or tissue. Analyte capture coatings or elements can additionally include, for example, chemical linkers or other chemical moieties that can be attached to a microfilter and which exhibit selective binding activity toward a target analyte. Attachment to a microfilter can be performed by, for example, covalent or non-covalent interactions and can be reversible or essentially irreversible. Those moieties useful as an analyte capture coating or element can similarly be employed as an secondary binding partner so long as the secondary binding partner recognizes the analyte capture coating or element rather than the target analyte. Specific examples of an affinity binding reagent useful as a secondary binding partner is avidin, or streptavidin, or protein A where the analyte capture coating or element is conjugated with biotin or is an antibody, respectively. Similarly, selective binding of an analyte capture coatings or element to a target analyte also can be performed by, for example, covalent or non-covalent interactions. Specific examples of a biochemical analyte capture coating or element is an antibody. A specific example of a chemical analyte capture coating or element is a photoactivatable linker. Other analyte capture coatings or elements that can be attached to a microfilter and which exhibit selective binding to a target analyte are known in the art and can be employed in the device, apparatus or methods of the invention given the teachings and guidance provided herein.

One exemplary form of microfilters manufactured in accordance with exemplary aspects of the present invention (i) standard microfilters and (ii) nanosurface topography microfilters are coated with analyte capture elements.

One specific exemplary form of the microfilters are microfilters coated with antibodies against EpCAM, MUC-1, and other surface markers are to capture tumor cells from body fluids, such as blood, urine, bone marrow, bladder wash, rectal brushings, fecal matter, saliva, spinal and cerebral fluids, and other body fluids.

Another specific exemplary form of the microfilters coated with antibodies against CD24, CD44, CD133, CD166, and/or other surface markers are to capture epithelial-mesenchymal transition (EMT) cells from body fluids, such as blood, urine, bone marrow, bladder wash, rectal brushings, fecal matter, saliva, cord blood, spinal and cerebral fluids, and other body fluids.

Another specific exemplary form of the microfilters coated with antibodies against CD34, and/or other surface markers are to capture stem cells from body fluids, such as peripheral blood and cord blood.

Filtration Applications of Smooth Microfilters and Nanosurface Microfilters

Exemplary applications of the various forms of microfilters manufactured in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) are for processing body fluids, such as blood, urine, bone marrow, bladder wash, rectal brushings, fecal matter, saliva, spinal and cerebral fluids, and other body fluids. The analyte of interests in the body fluids are circulating tumor cells, tumor cells, epithelial-mesenchymal transition (EMT) cells, CAMLs, white blood cells, B-cells, T-cells, circulating fetal cells in mother's blood, circulating endothelial cells, stromal cells, mesenchymal cells, endothelial cells, epithelial cells, stem cells, hematopoietic and non-hematopoietic cells, analytes bound to latex beads or an antigen-induced particle agglutination.

Another exemplary application of the microfilters manufactured in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) is capturing circulating cancer associated macrophage-like cells (CAMLs) from peripheral blood. CAMLs have the following characteristics:

- CAMLs have a large atypical nucleus; multiple individual nuclei can be found in CAMLs, though enlarged fused nucleoli approximately 14 µm to approximately 65 µm are common.
- CAMLs may express at least CK 8, 18 or 19, and the CK is diffused, or associated with vacuoles and/or ingested material. CAMLs express markers associated with the type of cancer. Those markers and CK are nearly uniform throughout the whole cell.
- CAMLs are most of the time CD45 positive.
- CAMLs are large, approximately 20 micron to approximately 300 micron in size.
- CAMLs come in five distinct morphological shapes (spindle, tadpole, round, oblong, or amorphous).
- If CAML express EpCAM, EpCAM is diffused, or associated with vacuoles and/or ingested material, and nearly uniform throughout the whole cell, but not all CAML express EpCAM, because some tumors express very low or no EpCAM.
- CAML express markers associated with the markers of the tumor origin; e.g., if the tumor is of prostate cancer origin and expresses PSMA, then CAML from this patient also expresses PSMA. Another example, if the primary tumor is of pancreatic origin and expresses PDX-1, then CAML from this patient also expresses PDX-1.
- CAMLs express monocytic markers (e.g. CD11c, CD14) and endothelial markers (e.g. CD146, CD202b, CD31).
- CAMLs also have the ability to bind Fc fragments.

Another exemplary application of a microfilter manufactured in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) is capturing circulating fetal cells in a mother's blood during weeks 11-12 weeks of pregnancy. Such fetal cells may include primitive fetal nucleated red blood cells. Fetal cells circulating in the peripheral blood of pregnant women are a potential target for noninvasive genetic analyses. They include epithelial (trophoblastic) cells, which are 14-60 µm in diameter, larger than peripheral blood leukocytes. Enrichment of circulating fetal cells followed by genetic diagnostic can be used for noninvasive prenatal diagnosis of genetic disorders using PCR analysis of a DNA target or fluorescence in situ hybridization (FISH) analysis of genes.

Another exemplary application of a microfilter manufactured in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) is collecting or enriching stromal cells, mesenchymal cells, endothelial cells, epithelial cells, stem cells, hematopoietic and non-hematopoietic cells, etc. from a blood sample, collecting tumor or pathogenic cells in urine, and collecting tumor cells in spinal and cerebral fluids. Another exemplary application is using the microfilter to collect tumor cells in spinal fluids. Another exemplary application is using the microfilter to capture analytes bound to latex beads or antigen caused particle agglutination whereby the analyte/latex bead or agglutinated clusters are captured on the membrane surface.

Another exemplary application of a microfilter formed in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) is for erythrocyte deformability testing. Red blood cells are highly flexible cells that will readily change their shape to pass through pores. In some diseases, such as sickle cell anemia, diabetes, sepsis, and some cardiovascular conditions, the cells become rigid and can no longer pass through small pores. Healthy red cells are typically 7.5 µm and will easily pass through a 3 µm pore membrane, whereas a cell with one of these disease states will not. In the deformability test, a microfilter having 5 µm apertures is used as a screening barrier. A blood sample is applied and the membrane is placed under a constant vacuum. The filtration rate of the cells is then measured, and a decreased rate of filtration suggests decreased deformability.

Another exemplary application of a microfilter formed in accordance with exemplary aspects of the present invention (e.g. (i) standard microfilters, (ii) nanosurface topography microfilters, (iii) standard microfilters coated with analyte capture elements, and (iv) nanosurface microfilters coated with analyte capture elements) is leukocyte/Red blood cell separation. Blood cell populations enriched for leukocytes (white blood cells) are often desired for use in research or therapy. Typical sources of leukocytes include whole peripheral blood, leukopheresis or apheresis product, or other less common sources, such as umbilical cord blood. Red blood cells in blood can be lysed. Then the blood is caused to flow through the microfilter with small pores to keep the leukocytes. Another exemplary application is using the microfilter for chemotaxis applications. Membranes are used in the study of white blood cell reactions to toxins, to determine the natural immunity in whole blood. Since immunity is transferable, this assay is used in the development of vaccines and drugs on white blood cells. Another exemplary application is using the microfilter for blood filtration and/or blood transfusion. In such applications, microfilters can be used to remove large emboli, platelet aggregates, and other debris.

What is claimed is:

1. A microfilter comprising:
a first polymer layer formed from an epoxy-based photo-definable dry film, wherein the first polymer layer has flexibility to be disposed on a roll and unrolled;
a plurality of first apertures each extending through the first polymer layer formed by exposing the first polymer layer to a UV light via an optical mask to obtain a selected shape of said apertures based on said optical mask, said first polymer layer forming at least a portion of said microfilter; and
a surface on said first polymer layer,
wherein said surface is
modified to include a rough nanosurface, and
modified to be hydrophilic with bonding sites on said surface for reagents.

2. The microfilter of claim 1 further comprising a second polymer layer formed from photo-definable dry film and having second apertures extending through the second polymer layer, wherein the second polymer layer has flexibility to be disposed on a roll and unrolled, and at least one of the first apertures and at least one of the second apertures define at least a portion of a passage extending through the first and second layers.

3. The microfilter of claim 1, wherein the surface is modified by changing of a surface energy, the polymer layer having the surface energy raised.

4. The microfilter of claim 1, wherein said first polymer layer has a uniform thickness of 5 to 100 microns.

5. The microfilter of claim 1, wherein said first polymer layer has a uniform thickness of 10 µm.

6. The microfilter of claim 1, wherein said selected shape of at least one of said apertures is one of round, oval, or rectangle.

7. The microfilter of claim 1, wherein said selected shape of said apertures is round with a diameter of 5-20 µm.

8. The microfilter of claim 1, wherein said surface is modified to include said rough nanosurface, and said rough nanosurface comprises said first polymer layer modified by an operation selected from the group consisting of changing of the surface energy, altering of the surface topography, and altering of the surface chemistry, and combinations thereof.

9. The microfilter of claim 1, wherein said epoxy-based photo-definable dry film is an epoxy-based negative photo-definable dry film.

* * * * *